(12) United States Patent
Spahn

(10) Patent No.: US 7,391,848 B2
(45) Date of Patent: Jun. 24, 2008

(54) METHOD AND X-RAY SYSTEM FOR TAKING X-RAY PICTURES OF AN EXAMINATION OBJECT IMAGED ON A DIGITAL X-RAY DETECTOR

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/352,217

(22) Filed: Feb. 13, 2006

(65) Prior Publication Data

US 2006/0188066 A1     Aug. 24, 2006

(30) Foreign Application Priority Data

Feb. 14, 2005    (DE) ................. 10 2005 006 658

(51) Int. Cl.
*G01T 1/24* (2006.01)
*H05G 1/64* (2006.01)
*H01L 27/146* (2006.01)

(52) U.S. Cl. ................. 378/98; 250/370.09; 250/587

(58) Field of Classification Search .............. 378/8, 378/19, 20, 62, 91, 95, 98, 98.8, 147–153, 378/204, 205, 210; 250/362, 369, 370.01, 250/370.08, 370.09, 371, 583, 584, 587
See application file for complete search history.

(56) References Cited

U.S. PATENT DOCUMENTS

| | | | | |
|---|---|---|---|---|
| 4,852,134 A * | 7/1989 | Kinanen et al. | ............. | 378/38 |
| 4,947,416 A * | 8/1990 | McFaul et al. | ............. | 378/146 |
| 5,426,684 A * | 6/1995 | Gaborski et al. | ............. | 378/62 |
| 5,815,596 A * | 9/1998 | Ahuja et al. | ............. | 382/173 |
| 6,173,033 B1 | 1/2001 | Klingenbeck-Regn et al. | | |
| 6,222,906 B1 * | 4/2001 | Sakaguchi et al. | ......... | 378/98.8 |
| 6,243,485 B1 * | 6/2001 | Murakami | .............. | 382/132 |
| 6,256,404 B1 * | 7/2001 | Gordon et al. | ............. | 382/131 |
| 6,393,100 B1 * | 5/2002 | Leeds et al. | ............. | 378/150 |
| 6,549,609 B1 * | 4/2003 | Iinuma et al. | ............. | 378/150 |
| 6,793,391 B2 * | 9/2004 | Zimmermann | ............. | 378/205 |
| 6,915,003 B2 * | 7/2005 | Oosawa | ............. | 382/130 |

(Continued)

FOREIGN PATENT DOCUMENTS

DE    197 21 535 C1    9/2001

(Continued)

OTHER PUBLICATIONS

German Search Report dated Dec. 27, 2005.

(Continued)

*Primary Examiner*—Edward J Glick
*Assistant Examiner*—Anastasia Midkiff
(74) *Attorney, Agent, or Firm*—Harness, Dickey & Pierce, P.L.C.

(57) ABSTRACT

In a method for quickly taking and evaluating X-ray pictures of an examination object imaged on a digital X-ray detector, the first step is for a partial imaging surface required for X-ray examination of the respective examination object to be automatically selected with reference to size and position from the entire imaging surface of the X-ray detector. After this, only the imaging data of the partial imaging surface that are compiled per examination are used as a basis for evaluation and/or display.

15 Claims, 1 Drawing Sheet

U.S. PATENT DOCUMENTS

| | | | |
|---|---|---|---|
| 2003/0118225 A1* | 6/2003 | Sako | 382/132 |
| 2003/0179851 A1* | 9/2003 | Ishikawa | 378/62 |
| 2004/0091083 A1* | 5/2004 | Jurgen | 378/205 |
| 2004/0125921 A1 | 7/2004 | Allouche et al. | |
| 2004/0246479 A1* | 12/2004 | Cartlidge et al. | 356/335 |
| 2005/0121505 A1* | 6/2005 | Metz et al. | 235/375 |

FOREIGN PATENT DOCUMENTS

| | | |
|---|---|---|
| DE | 103 49 785 A1 | 5/2004 |
| EP | 0 742 536 BA | 9/2000 |
| EP | 0 736 842 B1 | 12/2003 |

OTHER PUBLICATIONS

Flachbilddetektoren in der Röntgendiagnostik (M. Spahn, V. Heer, R. Freytag) Zeitschrift Radiologie 43, 2004, Seite 340 bis 350 2004Q16956 DE.

* cited by examiner

METHOD AND X-RAY SYSTEM FOR TAKING X-RAY PICTURES OF AN EXAMINATION OBJECT IMAGED ON A DIGITAL X-RAY DETECTOR

The present application hereby claims priority under 35 U.S.C. §119 on German patent application number DE 10 2005 006 658.5 filed Feb. 14, 2005, the entire contents of which is hereby incorporated herein by reference.

FIELD

The invention generally relates to a method for taking X-ray pictures of an examination object irradiated by an X-ray beam and imaged on an active imaging surface, constructed from pixel elements, of an X-ray detector, and/or to an X-ray system.

BACKGROUND

Known in X-ray imaging for the purpose of taking digital X-ray pictures of an examination object are X-ray detectors that are designed as flat image detectors. Further, X-radiation is converted into electric charge by a scintillator or a direct converter layer, and is subsequently read out electronically by way of active readout matrices. Subsequently, the imaging data representing the examination results are transmitted to an evaluation and display apparatus and further processed for the purpose of compiling images.

The readout matrices include a large number of pixel elements (article entitled "Flachbilddetektoren in der Röntgendiagnostik" ["Flat image detectors in X-ray diagnostics"] by M. Spahn, V. Heer, R. Freytag, published in the journal Radiologe 43, 2004, pages 340 to 350). Since these generally have to be read out, chiefly as regards dynamic X-ray systems, that is to say X-ray systems that compile a series of pictures, at a high frequency such as, for example, 30 images per second and with a high gray-scale resolution, large data quantities arise that are to be transmitted to the evaluation and display apparatus and are to be processed.

The large data quantities can lead to data bottlenecks that, in turn, reduce the rates at which the data are read out and transmitted. The use of more powerful electronic components is complicated and involves high volumes, and is attended by disadvantages such as, for example, high costs or increased production of heat. In order to limit the data quantities and raise the data transmission rates, there are also known X-ray detectors which have predefined zoom stages centered with reference to the imaging surface, and in the case of which only imaging data of the partial imaging surface that targeted in the zoom are transmitted to an evaluation and display apparatus.

SUMMARY

It is an object of at least one embodiment of the present invention, particularly in the case of dynamic X-ray systems, to be able to take X-ray pictures of an examination object imaged on a digital X-ray detector in a quick and simple way and as flexibly as possible, and evaluate them.

An object may be achieved by a method and/or by an X-ray system.

In the case of the method according to at least one embodiment of the invention, it is possible in advance and with low outlay to limit the X-ray detector imaging surface to be taken into account for compiling imaging data to the actual partial imaging surface illuminated by the examination object by determining the coverage of the imaging surface by the examination object, or by having recourse to the X-ray beam illuminating the examination object, and thus to substantially reduce the data quantity to be processed for the examination.

Moreover, a high level of flexibility with regard to position, type and size of the partial imaging surface for the purpose of adaptation to the examination object is ensured by virtue of the fact that every area of the imaging surface that is possible with reference to size and position can be selected as partial imaging surface.

According to a first refinement of at least one embodiment of the invention, for the purpose of automatically selecting the partial imaging surface, the first step is to read out the entire imaging surface with regard to its coverage by the examination object in such a way that the area of the imaging surface read out that is covered by the examination object is determined by way of imaging processing, and then this area is selected as partial imaging surface for the examination. In this way, which is well suited for picturing hands, for example, the required partial imaging surface can be adapted to the examination object with particular precision, can be evaluated with regard to its imaging data, and can be used instead of the entire imaging surface as a basis for subsequent evaluation of the examination.

According to a second, alternative refinement of at least one embodiment of the invention, for the purpose of automatically selecting the partial imaging surface at first the focus/stop/X-ray geometry defining the X-ray beam is set up for irradiating the examination object, and subsequently the partial imaging surface for the examination is calculated from the focus/stop/X-ray geometry, in particular from the aperture angle of the X-ray beam and the distance from the focus to the imaging surface. It is possible with the aid of this refinement to achieve a partial imaging surface that is well adapted to the existing illumination of the examination object by the X-ray beam, without previously reading out the entire imaging surface of the X-ray detector.

The automatic selection of the partial imaging surface is advantageously executed exclusively in the X-ray detector; consequently, imaging data are not transmitted to imaging and/or display apparatuses until after the selection.

BRIEF DESCRIPTION OF THE DRAWINGS

At least one embodiment of the invention, and further advantageous refinements in accordance with features, are explained below in more detail in the detailed description and drawings, with the aid of schematically illustrated example embodiments, without thereby limiting the invention to these example embodiments; in the drawings.

DETAILED DESCRIPTION OF THE EXAMPLE EMBODIMENTS

Figure 1:
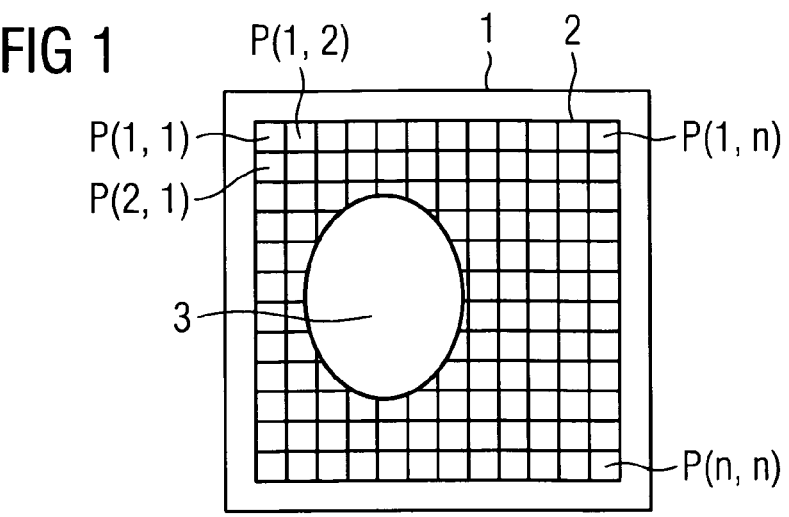
FIG. 1 shows a plan view of an imaging surface of a flat detector with an examination object laid thereon.
Figure 2:
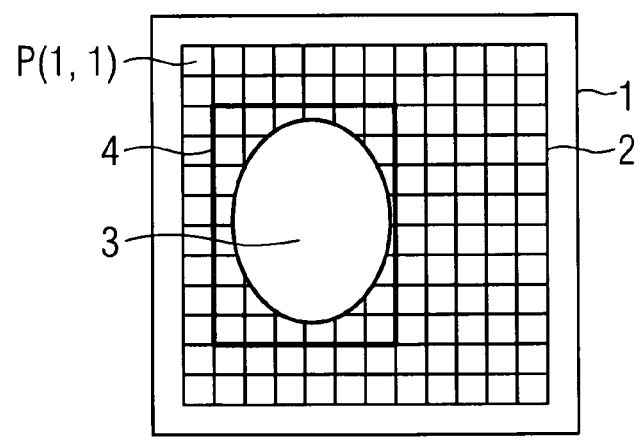
FIG. 2 shows a plan view of the imaging surface in accordance with FIG. 1 of an X-ray detector with a partial imaging surface determined according to at least one embodiment of the invention in accordance with the size and position of the examination object.
Figure 3:
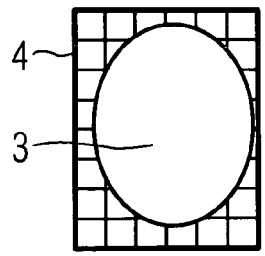
FIG. 3 shows a plan view of the partial imaging surface selected in accordance with FIG. 2 for examination.

FIG. 1 shows a plan view of an imaging surface 2, constructed from a matrix of n*n pixel elements (P(1,1), . . . , P(1,n), . . . , P(2,1), . . . , P(n,n)), of a digital X-ray detector 1. The sensor surface of the X-ray detector 1, which is available to a maximum extent for converting X-radiation into imaging data, is denoted as imaging surface 2. An examination object 3 provided for X-ray examination is located on the X-ray detector 1. Before the beginning of the actual X-ray examination, the X-ray detector 1 automatically selects a partial imaging surface 4—illustrated in FIG. 2 and FIG. 3—required with reference to size and position for the X-ray examination of the examination object 3. The automatic selection facilitates the X-ray examination for the user.

According to refinements of at least one embodiment of the invention, two methods explained in more detail below are provided for automatically selecting the partial imaging surface 4. According to a first refinement of at least one embodiment of the invention, for the purpose of automatically selecting the partial imaging surface 4 image processing is carried out, particularly inside the detector, in order to determine the area on the imaging surface 2 previously read out simply that is covered by the examination object 3.

To this end, the entire imaging surface is firstly read out without being transmitted to an evaluation and/or display apparatus. Image processing, particularly inside the detector, is used to ascertain the area of the imaging surface 2 read out that is covered by the examination object 3. This can be performed, for example, by determining the outer contours of the examination object 3 on the basis of brightness matches between maximum and minimum brightnesses of the gray tones of the X-ray picture by way of known image processing methods.

Subsequently, the area of the imaging surface 2 covered by the examination object 3 is selected as a partial imaging surface 4 for the examination. It is provided for this purpose to define as partial imaging surface 4 the smallest rectangular surface made from pixel elements (P(1,1), . . . P(n,n)) that contains the examination object 3 including its outer contour. However, it can also be provided to select as partial imaging surface 4 the smallest surface made from pixel elements (P(1,1), . . . P(n,n)) that completely contains the examination object 3 including its outer contour.

Figure 4:
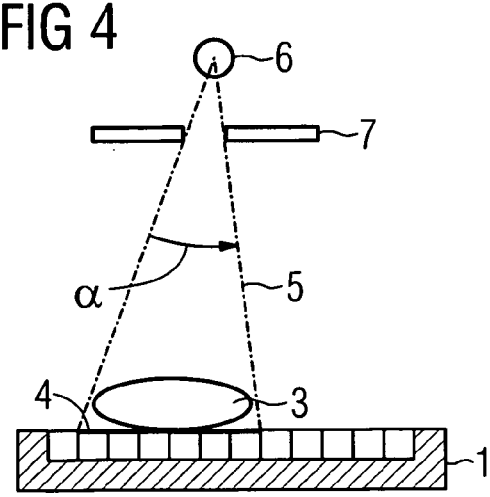
FIG. 4 shows a side view of an X-ray system with a partial imaging surface on the X-ray detector determined on the basis of the focus/stop/X-ray geometry.

According to a further refinement of at least one embodiment of the invention, the beam geometry of the X-ray beam 5 directed onto the examination object 3 is used, as shown in FIG. 4, as a basis for automatically selecting the partial imaging surface 4; the partial imaging surface 4 for the X-ray examination is calculated from the focus/stop/X-ray beam geometry of this X-ray beam 5. The calculation is expediently based on the positions of the focus 6 of the X-ray beam 5 and of the beam stop 7, the aperture angle α of the X-ray beam 5, and the corresponding distances between the X-ray detector 1, focus 6 and beam stops 7. These geometric data are, for example, transmitted by the X-ray system to the X-ray detector 1; the latter carries out the calculation inside the detector, for example by means of an integrated calculation unit.

Subsequently, the calculated area is selected as partial imaging surface 4. To this end, it is possible by analogy with the previously explained selection method to select the smallest or the smallest rectangular surface made from pixel elements (P(1,1), . . . , P(n,n)) as partial imaging surface 4 that completely contains the calculated area.

Following upon the selection, the actual X-ray examinations are carried out starting from the partial imaging surface 4, and the imaging data of the partial imaging surface 4 that are compiled for each X-ray examination are used as a basis for evaluation and/or display. According to one refinement of at least one embodiment of the invention, for the examination exclusively imaging data of the partial imaging surface 4 is read out electronically by way of active readout matrices of the X-ray detector 1 and transmitted to an evaluation and/or display apparatus communicatively connected to the X-ray detector 1. However, it can also be provided to read out imaging data of the entire imaging surface 2 for the examination, and to transmit exclusively the imaging data of the partial imaging surface 4 to an evaluation and/or display apparatus communicatively connected to the X-ray detector 1.

Particularly with dynamic X-ray systems, in the case of which series of X-ray pictures must be transmitted and be pictorially illustrated by a display apparatus, a reduction, possible on the basis of the invention, of the data quantity to be processed for the X-ray examination leads to a substantial reduction in the data flow. The position of the partial imaging surface 4 within the entire imaging surface 2 is also expediently transmitted to the evaluation and/or display apparatus. To this end, it is possible, for example, to transmit the positions of the pixel elements (P(1,1), . . . , P(1,n), . . . , P(2,1), . . . , P(n,n) contained on the partial imaging surface 4.

At least one embodiment of the invention may be summarized briefly as follows: for the purpose of quickly taking and evaluating X-ray pictures of an examination object 3 imaged on a digital X-ray detector 1, the first step is for a partial imaging surface 4 required for X-ray examination of the respective examination objects to be automatically selected with respect to size and position from the entire imaging surface 2 of the X-ray detector 1, after which only the imaging data of the partial imaging surface 4 that are compiled per examination are used as a basis for evaluation and/or display.

Any of the aforementioned methods may be embodied in the form of a system or device, including, but not limited to, any of the structure for performing the methodology illustrated in the drawings.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method involving an examination object irradiated by an X-ray beam and imaged onto an active imaging surface of a digital X-ray detector, the method comprising:

automatically selecting a partial imaging surface required for an X-ray examination of the respective examination object, with reference to size and position of the partial imaging surface, the automatic selection of the partial imaging surface being executed exclusively in the X-ray detector, and the automatically selecting of the partial imaging surface including, first, reading out the entire imaging surface, subsequently determining the area covered by the examination object by use of image processing, and selecting the area covered by the examination object as the partial imaging surface for the examination; and using only the imaging data of the partial imaging surface that are compiled per examination, as a basis for at least one of subsequent evaluation and display of the imaging data.

2. A method involving an examination object irradiated by an X-ray beam and imaged onto an active imaging surface of a digital X-ray detector, the method comprising:

automatically selecting a partial imaging surface reciuired for an X-ray examination of the examination object, with reference to size and position of the partial imaging, the automatic selection of the partial imaging surface being executed exclusively in the X-ray detector, and the automatically selecting of the partial imaging surface including, first, transmitting to the detector a focus/stop/X-ray geometry defining the X-ray beam, for irradiating the examination object, and subsequently calculating, by a calculation unit integrated into the detector, the partial imaging surface for the examination, from the focus/stop/X-ray geometry; and using only the imaging data of the partial imaging surface that are compiled per examination, as a basis for at least one of subsequent evaluation and display of the imaging data.

3. The method as claimed in claim 1, wherein only the imaging data of the partial imaging surface are read out after the automatic selection of the partial imaging surface.

4. The method as claimed in claim 1, wherein only the imaging data of the partial imaging surface are transmitted to at least one of an evaluation and display apparatus after the automatic selection of the partial imaging surface.

5. The method as claimed in claim 1, wherein the position of the partial imaging surface on the imaging surface is transmitted to at least one of an evaluation and a display apparatus.

6. An X-ray system, comprising:
a digital X-ray detector including an active imaging surface for X-ray imaging of an examination object irradiated by an X-ray beam, a partial imaging surface of the active imaging surface for an X-ray examination of the respective examination object being selected automatically with reference to size and position of the partial imaging surface, and imaging data, compiled per examination, of the partial imaging surface being used as a basis for at least one of subsequent evaluation and display of the imaging data; wherein
the automatic selection of the active imaging surface is executed exclusively in the X-ray detector and the automatic selection includes,
first, reading out the entire imaging surface,
subsequently determining the area covered by the examination object-by use of image processing, and
selecting the area covered by the examination object as partial imaging surface for the examination.

7. The method as claimed in claim 1, wherein automatically selecting the partial imaging surface further includes,
first, setting up a focus/stop/X-ray geometry defining the X-ray beam, for irradiating the examination object, and
subsequently calculating the partial imaging surface for the examination, from the focus/stop/X-ray geometry.

8. The method as claimed in claim 2, wherein automatically selecting the partial imaging surface includes,
subsequently calculating the partial imaging surface for the examination, from an aperture angle of the X-ray beam and the distance from the focus to the imaging surface.

9. The method as claimed in claim 7, wherein automatically selecting the partial imaging surface further includes,
subsequently calculating the partial imaging surface for the examination, from an aperture angle of the X-ray beam and the distance from the focus to the imaging surface.

10. The method as claimed in claim 2, wherein only the imaging data of the partial imaging surface are read out after the automatic selection of the partial imaging surface.

11. The method as claimed in claim 2, wherein only the imaging data of the partial imaging surface are transmitted to at least one of an evaluation and display apparatus after the automatic selection of the partial imaging surface.

12. The method as claimed in claim 2, wherein the position of the partial imaging surface on the imaging surface is transmitted to at least one of the evaluation and display apparatus.

13. An X-ray system, comprising:
a digital X-ray detector including an active imaging surface for X-ray imaging of an examination object irradiated by an X-ray beam;
means for automatically selecting a partial imaging surface required for an X-ray examination of the respective examination object, with reference to size and position of the partial imaging surface; and
means for using only the imaging data of the partial imaging surface that are compiled per examination, as a basis for at least one of subsequent evaluation and display of the imaging data; wherein
the means for automatically selecting the partial imaging surface is included in the X-ray detector, the automatically selecting of the partial imaging surface including,
first, reading out the entire imaging surface,
subsequently determining the area covered by the examination object-by use of image processing, and
selecting the area covered by the examination object as partial imaging surface for the examination.

14. An X-ray system, comprising:
a digital X-ray detector including an active imaging surface for X-ray imaging of an examination object irradiated by an X-ray beam;
means for automatically selecting a partial imaging surface required for an X-ray examination of the respective examination object, with reference to size and position of the partial imaging surface; and
means for using only the imaging data of the partial imaging surface that are compiled per examination, as a basis for at least one of subsequent evaluation and display of the imaging data; wherein
the means for automatically selecting the partial imaging surface is included in the X-ray detector, and the automatically selecting of the partial imaging surface includes,
first, transmitting to the detector a focus/stop/X-ray geometry defining the X-ray beam, for irradiating the examination object, and
subsequently calculating, by a calculation unit integrated into the detector, the partial imaging surface for the examination, from the focus/stop/X-ray geometry.

15. An X-ray system, comprising:
a digital X-ray detector including an active imaging surface for X-ray imaging of an examination object irradiated by an X-ray beam, a partial imaging surface of the active imaging surface for an X-ray examination of the respective examination object being selected automatically with reference to size and position of the partial imaging surface, and imaging data, compiled per examination, of the partial imaging surface being used as a basis for at least one of subsequent evaluation and display of the imaging data; wherein
the automatic selection of the active imaging surface is executed exclusively in the X-ray detector, and the automatic selection of the partial imaging surface includes,
first, transmitting to the detector a focus/stop/X-ray geometry defining the X-ray beam, for irradiating the examination object, and
subsequently calculating, by a calculation unit integrated into the detector, the partial imaging surface for the examination, from the focus/stop/X-ray geometry.

* * * * *